(12) United States Patent
Matthison-Hansen et al.

(10) Patent No.: US 11,033,287 B2
(45) Date of Patent: Jun. 15, 2021

(54) GRASPING TOOL

(71) Applicant: Coloplast A/S, Humlebaek (DK)

(72) Inventors: Kaspar Matthison-Hansen, Aalsgaarde (DK); Thomas Bachgaard Jensen, Copenhagen (DK); Jakob Boennelykke Kristensen, Oelstykke (DK)

(73) Assignee: Coloplast A/S, Humlebaek (DK)

( * ) Notice: Subject to any disclaimer, the term of this patent is extended or adjusted under 35 U.S.C. 154(b) by 208 days.

(21) Appl. No.: 15/574,847

(22) PCT Filed: May 24, 2016

(86) PCT No.: PCT/DK2016/050142
§ 371 (c)(1),
(2) Date: Nov. 17, 2017

(87) PCT Pub. No.: WO2016/188531
PCT Pub. Date: Dec. 1, 2016

(65) Prior Publication Data
US 2018/0125514 A1     May 10, 2018

(30) Foreign Application Priority Data
May 27, 2015   (DK) ............................ PA 2015 70312

(51) Int. Cl.
*A61B 17/22*    (2006.01)
*A61B 17/30*    (2006.01)
*A61M 27/00*   (2006.01)
*A61B 17/00*    (2006.01)
*A61B 17/29*    (2006.01)
(Continued)

(52) U.S. Cl.
CPC ........ *A61B 17/22031* (2013.01); *A61B 17/30* (2013.01); *A61B 2017/00296* (2013.01); *A61B 2017/22035* (2013.01); *A61B 2017/2905* (2013.01); *A61B 2017/301* (2013.01);
(Continued)

(58) Field of Classification Search
CPC .............. A61B 17/22031; A61B 17/30; A61B 2017/301; A61B 2017/2905; A61B 2017/00296; A61B 2017/22035; A61F 2002/9528; A61F 2002/047
See application file for complete search history.

(56) References Cited

U.S. PATENT DOCUMENTS 3,653,389 A    4/1972   Shannon
4,418,694 A   12/1983   Beroff et al.
(Continued)

FOREIGN PATENT DOCUMENTS

CN     202235791 U     5/2012
CN     202477780 U    10/2012
(Continued)

*Primary Examiner* — Richard G Louis
(74) *Attorney, Agent, or Firm* — Coloplast Corp., Coloplast A/S; Nick Baumann

(57) ABSTRACT

A grasping tool (20) for removing a stent from the body of a patient. The grasping tool has a grasping head (38) forming two jaws connected to each other and configured to be shifted between an open state and a closed state. Each jaw includes three portions having different thicknesses. The grasping tool is configured to obtain sufficient holding force between the jaws while requiring reduced operating force of the tool. A method for removing a stent from a patient is also disclosed.

22 Claims, 14 Drawing Sheets

(51) Int. Cl.
*A61F 2/04* (2013.01)
*A61F 2/95* (2013.01)

(52) U.S. Cl.
CPC . *A61F 2002/047* (2013.01); *A61F 2002/9528* (2013.01); *A61M 27/008* (2013.01)

(56) References Cited

U.S. PATENT DOCUMENTS

| | | | |
|---|---|---|---|
| 4,449,530 A | 5/1984 | Bendel et al. | |
| 4,957,500 A * | 9/1990 | Liang | A61B 17/02 606/157 |
| 5,062,846 A | 11/1991 | Oh et al. | |
| 5,147,378 A | 9/1992 | Markham | |
| 5,499,997 A * | 3/1996 | Sharpe | A61B 17/221 606/205 |
| 5,722,989 A | 3/1998 | Fitch et al. | |
| 5,891,156 A | 4/1999 | Gessner et al. | |
| 2002/0045909 A1 * | 4/2002 | Kimura | A61B 17/083 606/151 |
| 2002/0099387 A1 | 7/2002 | Gauderer et al. | |
| 2002/0133178 A1 * | 9/2002 | Muramatsu | A61B 17/1227 606/142 |
| 2002/0143387 A1 | 10/2002 | Soetikno et al. | |
| 2004/0078044 A1 | 4/2004 | Kear et al. | |
| 2005/0070758 A1 | 3/2005 | Wells et al. | |
| 2005/0080440 A1 | 4/2005 | Durgin et al. | |
| 2005/0107809 A1 | 5/2005 | Litscher et al. | |
| 2005/0143767 A1 | 6/2005 | Kimura et al. | |
| 2006/0155308 A1 | 7/2006 | Griego | |
| 2008/0306491 A1 | 12/2008 | Cohen et al. | |
| 2010/0152753 A1 | 6/2010 | Menn et al. | |
| 2011/0039967 A1 | 2/2011 | Wilson et al. | |
| 2011/0295314 A1 | 12/2011 | Staud | |
| 2011/0301606 A1 * | 12/2011 | Kerr | A61B 18/1445 606/52 |
| 2011/0319710 A1 | 12/2011 | Phillips-Hungerford et al. | |
| 2012/0083803 A1 | 4/2012 | Patel et al. | |

FOREIGN PATENT DOCUMENTS

| | | |
|---|---|---|
| DE | 29619310 U1 | 2/1997 |
| EP | 0793944 A1 | 9/1997 |
| EP | 1547529 A1 | 6/2005 |
| GB | 949012 A | 2/1964 |
| GB | 2054730 A1 | 2/1981 |
| JP | 62053645 A2 | 3/1987 |
| JP | 2004121484 A2 | 4/2004 |
| WO | 9320759 A1 | 10/1993 |
| WO | 9420025 A1 | 9/1994 |
| WO | 9638092 A1 | 12/1996 |
| WO | 13130445 A1 | 9/2013 |
| WO | 2014172503 A1 | 10/2014 |

* cited by examiner

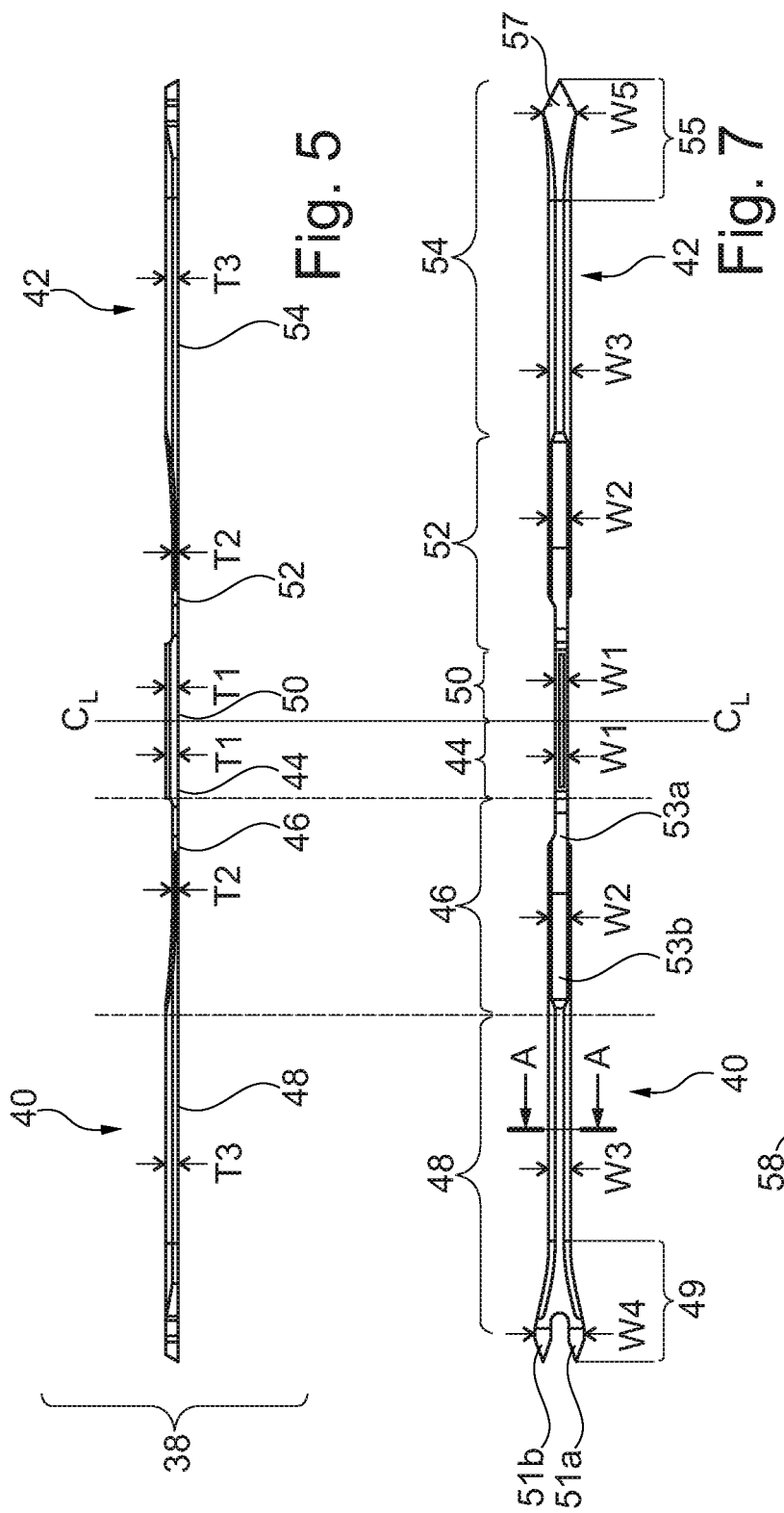

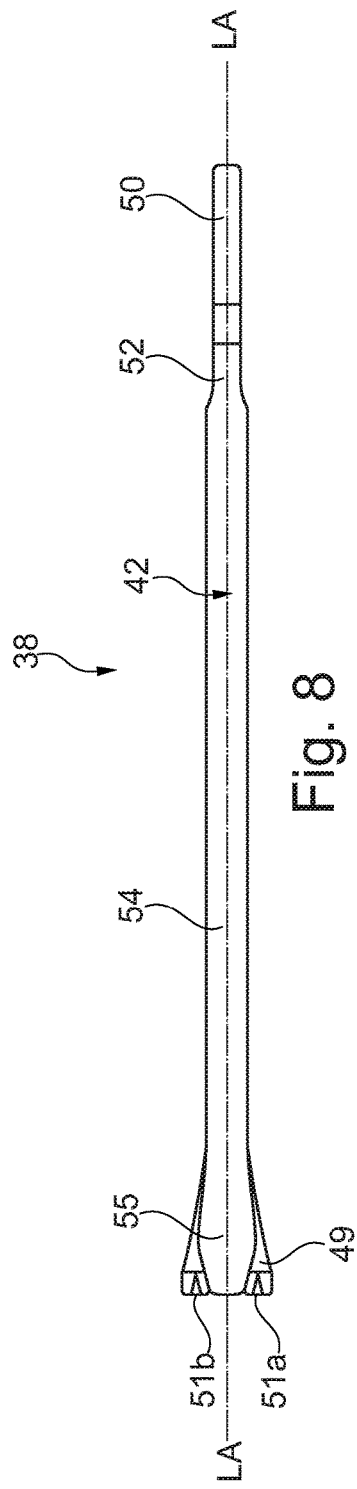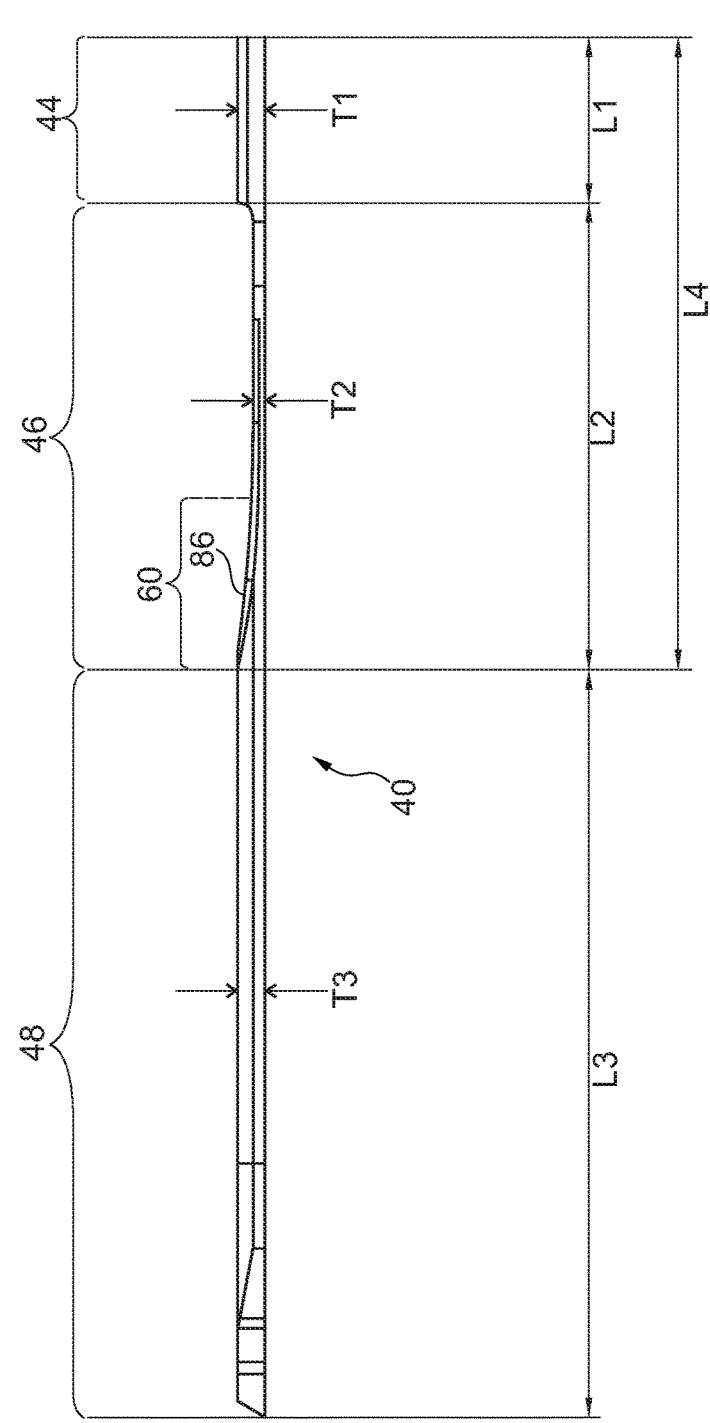
Fig. 8
Fig. 6

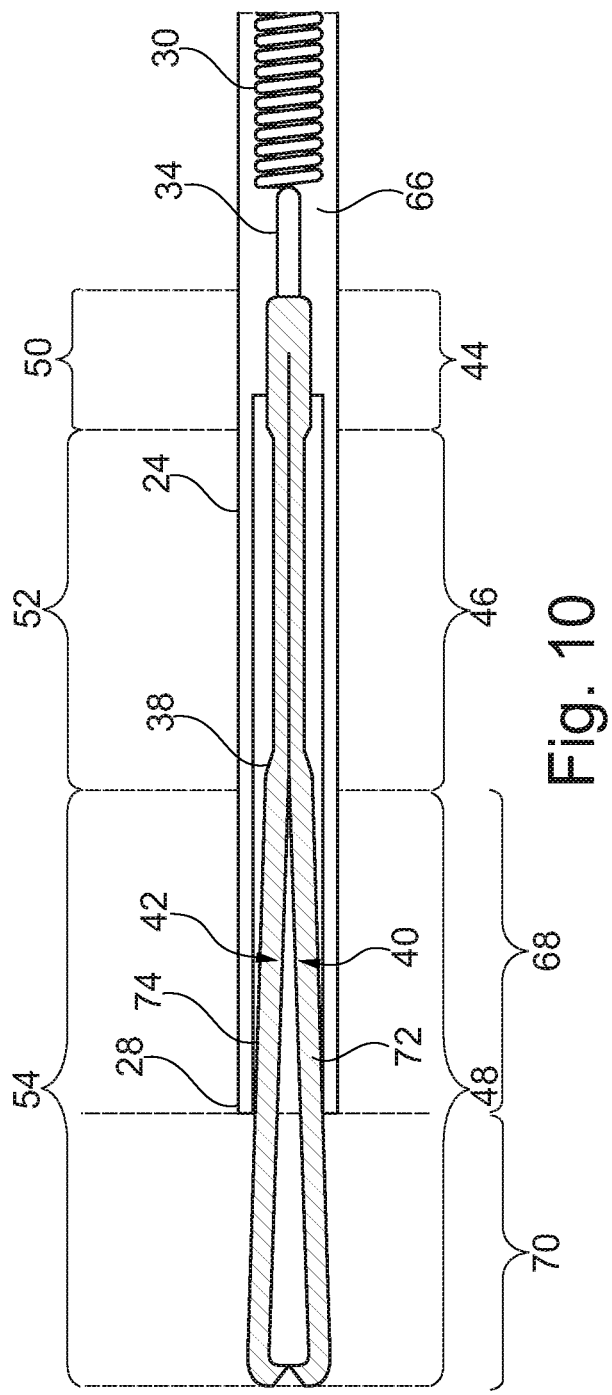
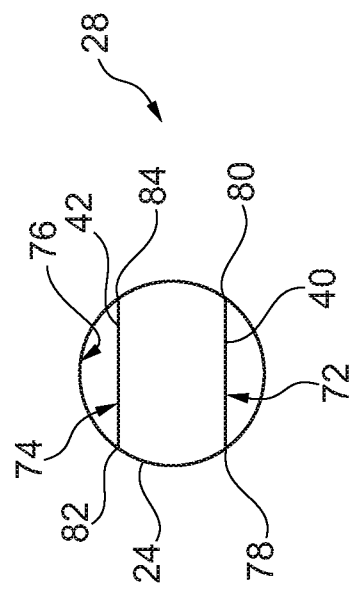
Fig. 10
Fig. 10A

GRASPING TOOL

BACKGROUND

A stent is a tube or other device placed in the body of a patient to create a passage. Some surgical procedures require a stent to be placed temporarily in the body of a patient such as during a healing period after surgery. One example is a ureteral stent placed in a ureter after a kidney stone removal procedure to secure a flow path for urine from the kidney to the bladder during the healing period. Often this stent is a JJ-stent, or pigtail stent, having first and second ends each shaped as the letter "J" (or resembling a pigtail). When the healing period is over, the ureteral stent must be removed from the patient. The normal procedure for removing the ureteral stent requires use of an endoscope and a grasper tool. The grasper tool must provide a holding force sufficient to securely grip the stent during removal. While the stent removal procedure in terms of patient involvement is often very short, preparation of the endoscope and grasper tool for the procedure, including sterilization after each use, is bothersome, time consuming and expensive. Patients and health care personnel would welcome improvements in endoscopes and graspers.

SUMMARY

One aspect of the present disclosure provides a grasping tool for removing a stent from a patient according to claim 1.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. Some figures are side views of a tubular component such as a sheath or insertion tube for which views it is to be understood that a portion facing the observer is removed for illustration purposes. The elements of the drawings are not necessarily to scale relative to each other.

FIG. 5 is a side view of one embodiment of a grasping head.

FIG. 6 is an enlarged side view of one embodiment of a first jaw of the grasping head.

FIG. 7 is a top view of one embodiment of the grasping head of FIG. 5.

FIG. 7A is a cross section taken along the line A-A in FIG. 7.

FIG. 8 is a top view of one embodiment of the grasping head of FIG. 4.

FIG. 10 is a side view of one embodiment of a grasping head.

FIG. 10A is an enlarged end view of one embodiment of the grasping tool.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

In this disclosure the term "body cavity" includes generally tubular body members such as, but not limited to, a ureter, a urethra, a colon and an ileum.

Unless specifically stated otherwise, the term "end" in this specification means an end portion of a thing, i.e. a portion that extends from the very endpoint of the thing in a direction towards a midpoint of the thing.

Embodiments provide a grasping tool that is useful for removing stents from a body cavity of a patient. Embodiments provide a grasping tool that is particularly useful for removing ureteral stents from a ureter of a patient via the patient's bladder and urethra.

Embodiments provide a grasping tool that is configured to obtain maximum holding force while requiring minimal operating force. Embodiments provide a grasping tool with two jaws each having a portion with reduced thickness to obtain increased spring properties of the jaws. Embodiments provide a grasping tool having cooperating jaws configured to close firmly around a stent while requiring a reduced force to close the jaws.

In one aspect, the present disclosure relates to a grasping tool for removing a stent from a patient.

Figure 1:
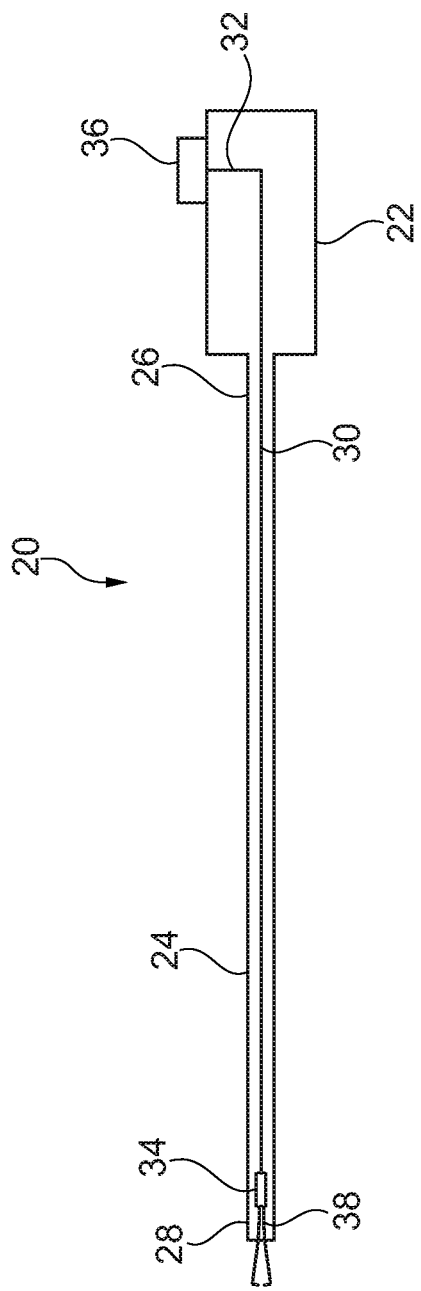
FIG. 1 is a side view of one embodiment of a grasping tool.

FIG. 1 is a side view of one embodiment of a grasping tool 20 (in the following also referred to as simply the "tool"). FIG. 1 shows the tool 20 in a closed state. In one embodiment, the tool 20 comprises a handle housing 22 forming a proximal portion of the tool. The tool 20 includes a sheath 24 having a first proximal end 26 and a first distal end 28.

In one embodiment, the first proximal end 26 is connected to the handle housing 22. In one embodiment, the tool 20 comprises a motion transfer member 30 that is movable within the sheath 24. The motion transfer member 30 has a second proximal end 32 and a second distal end 34. In one embodiment, the motion transfer member 30 is a wire. In one embodiment, the second proximal end 32 is connected to a tool operating member 36 provided on the handle housing 22. In one embodiment, the second distal end 34 of the motion transfer member 30 is connected to a grasping head 38 of the tool 20. In one embodiment, the tool operating member 36 is engaged with the handle housing 22 such as to be movable along a portion of the handle housing 22.

Figure 2:
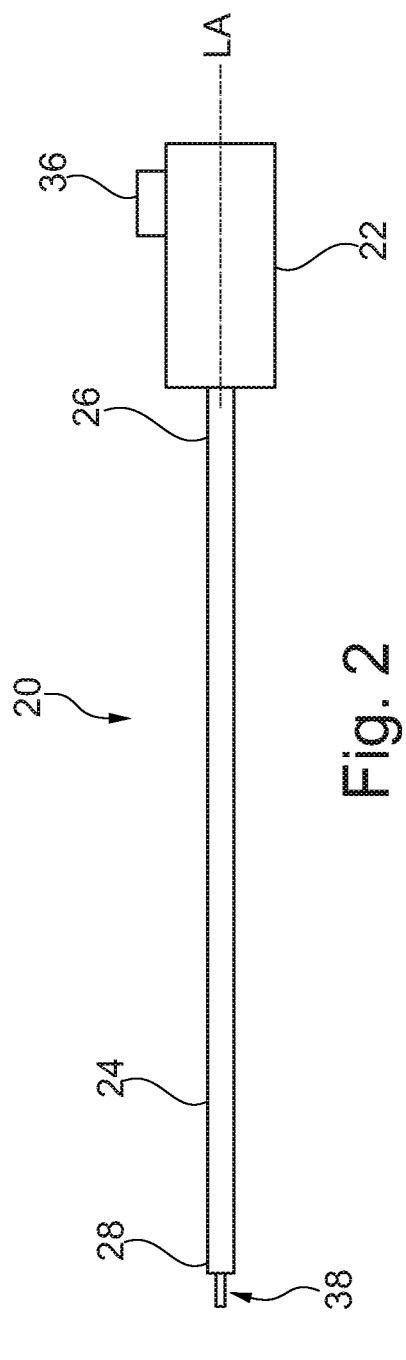
FIGS. 2 and 3 are side views of one embodiment of a grasping tool.
Figure 3:
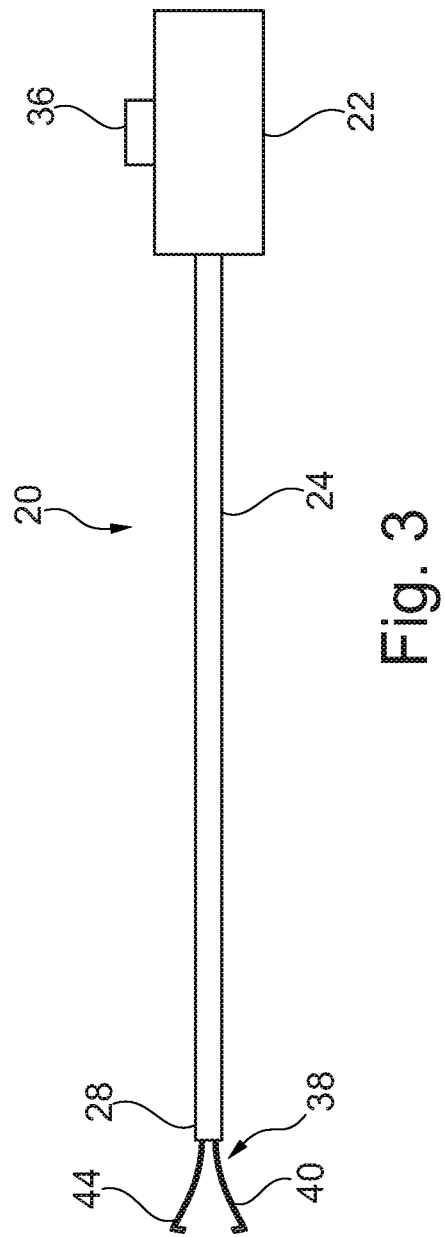

FIGS. 2 and 3 are side views of one embodiment of the tool 20. FIG. 2 shows the tool 20 in a closed state and FIG. 3 shows the tool 20 in an open state. As best observed in FIG. 3, in one embodiment, the grasping head 38 comprises a first jaw 40 and a second jaw 42. The first and second jaws are configured to be shifted between the closed and the open state by actuating the tool operating member 36. In one embodiment, actuating the tool operating member 36 moves the motion transfer member 30 relative to the sheath 24 such that the grasping head 38 moves out of an opening at the distal end 28 of the sheath 24 to shift the first and second jaws 40, 42 to the open state. In one embodiment, the actuation of the tool operating member 36 includes moving the tool operating member 36 along a longitudinal extent of the handle housing 22. In one embodiment, the actuation of the tool operating member 36 includes pressing the tool operating member 36 towards a center axis CA of the handle housing 22. Other ways of facilitating actuation of the tool operating member 36 are acceptable.

Figure 4:
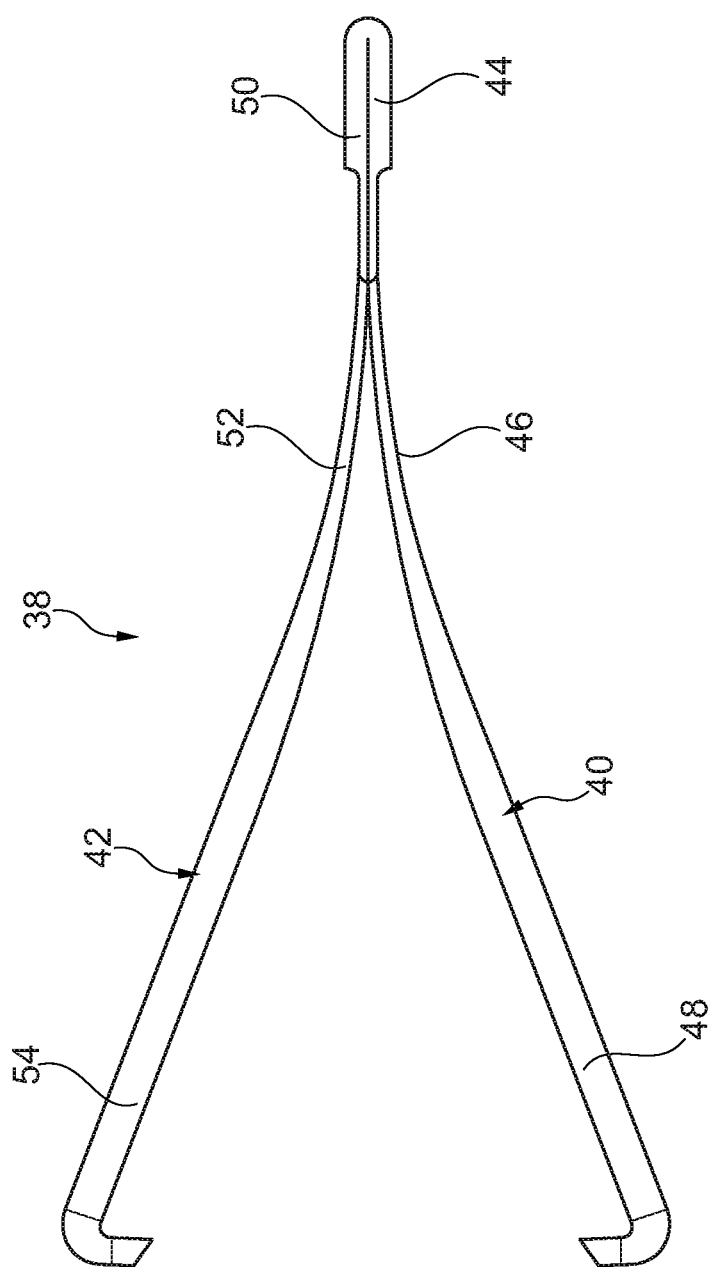
FIG. 4 is an enlarged side view of one embodiment of a grasping head of a grasping tool.

FIG. 4 is an enlarged side view of one embodiment of the grasping head 38 of the tool 20. The first jaw 40 includes a connecting portion 44, an intermediate portion 46 and a gripping portion 48. Similarly, the second jaw 42 includes a connecting portion 50, an intermediate portion 52 and a gripping portion 54. The jaws 40, 42 of the grasping head 38 are connected to each other at the connecting portion 44, 50. In one embodiment, the connecting portions 44, 50 are welded together.

FIG. 5 is a side view of one embodiment of the grasping head 38 in a situation where the grasping head is not finalized, i.e. it has not undergone all steps of manufacture to arrive the configuration shown in FIG. 4. In one embodiment, the grasping head 38 is manufactured from a single blank being shaped into the final shape of the grasping head 38 shown in FIG. 4 having a first thickness T1 of the connecting portion 44, 50, a second thickness T2 of the intermediate portion 46, 52, and a third thickness T3 of the gripping portion 48, 54. In one embodiment, the single blank is made from a suitable metal strip. One suitable process for manufacturing the grasping head 38 is progressive stamping which include (but is not limited to) partial processes such as punching, coining and bending. In one example, a feeding system pushes a strip of metal through stations of a progressive stamping die, wherein the individual stations performs one or more operations on the strip. Ultimately, the finished part, such as a grasping head, is separated from the carrying web of metal. In embodiments, suitable materials for the jaws 40, 42 of the grasping head 38 include stainless steel such as, but not limited to, the types AISI 304, AISI 316, 17-7 PH AISI 631.

In FIG. 5, the first jaw 40 corresponds to the left side of a centerline CL of the grasping head 38 and the second jaw 42 corresponds to the right side of the centerline CL. In one embodiment, the second thickness T2 is less (or smaller) than the third thickness T3. Providing the intermediate portion 46, 52 of a jaw 40, 42 with a lesser thickness T2 than the thickness T3 provides a grasping head 38 that requires less initial force to shift from the open state to the closed state. In one embodiment, the thickness T1 of the connecting portion 44, 50 is substantially identical to the third thickness T3 of the gripping portion 48, 54. By the term "substantially identical" is meant that the thicknesses T1 and T3 do not vary from each other by other than normal manufacturing tolerances. The reduced thickness T2 of the intermediate portion 46, 52 furthermore helps provide flexibility of the grasping head 38 in a location where it is particularly advantageous, thereby reducing the force needed to retract the grasping head 48 into the sheath 24. In turn, the larger thickness T3 of the gripping portion 48, 54 provides more stiffness where advantageous to help provide a firmer grip of the jaws 40, 42 of the grasping head 38 on a stent to be removed.

In one embodiment, the second thickness T2 of the intermediate portion 46, 52 is manufactured to be between ⅓ (one third) and ⅔ (two thirds) of the third thickness T3 of the gripping portion 48, 54.

FIG. 6 is an enlarged side view of one embodiment of the first jaw 40 of the grasping head 38, corresponding to an enlarged view of the left hand side of FIG. 5. In one embodiment, the intermediate portion 46 comprises a tapering zone 60 in which the thickness of the first jaw 40 transitions from the second thickness T2 of the intermediate portion 46 to the third thickness T3 of the gripping portion 48. Although FIG. 6 focuses only on the first jaw 40, it is to be understood that in embodiments the second jaw 42 likewise includes a tapering zone 60. One advantageous effect of the transition zone 60 is that, along with the lesser thickness T2 of the intermediate section 46, 52, it further reduces the force needed to shift the tool 20 from the open state to the closed state during initial closing of the jaws. That is, when the grasping head 38 begins to retract into the distal end 28 of the sheath 24 (FIG. 1) by actuating the tool operating member 36, the transition zone 60 effectively functions as a ramp for the sliding engagement between the respective jaw 40, 42 and the sheath 24. It further provides for the initial portion of the retraction sequence to be smooth, i.e. without any sudden jerks or staggered movements.

In one embodiment, a third length L3 of the gripping portion 48 exceeds a total combined length L4 of a first length L1 of the connecting portion 44 and a second length L2 of the intermediate portion 46 measured in a longitudinal direction of the grasping head 38. In one embodiment, the third length L3 of the gripping portion 48 is configured to be 4-6 times the first length L1 of the connecting portion 44 and the second length L2 of the intermediate portion 46 is configured to be 2-4 times the first length L1 of the connecting portion 44.

FIG. 7 is a top view of one embodiment of the grasping head 38 of FIG. 5 and, as in FIG. 5, shown in the not yet finalized shape of the grasping head. FIG. 7 shows the connection portion 44, 50, the intermediate portion 46, 52 and the gripping portion 48, 54 of each of the first and second jaws 40, 42. FIG. 7 further illustrates a relative widthwise extent of the connection, intermediate and gripping portions in embodiments of the grasping head 38. In one embodiment, respective connecting portions 44, 50 have a first width W1, respective intermediate portions 46, 52 have a second width W2 and respective gripping portions 48, 54 have a third width W3. In embodiments, a proximal segment 53a of the intermediate portion 46, 52 has a width that is less than the width W2 of a distal segment 53b of the intermediate portion 46, 52.

In one embodiment, the gripping portion 48 of the first jaw 40 is configured to have a plurality of (i.e. two or more) prongs 51a, 51b and the gripping portion 54 of the second jaw 42 is configured to have at least one prong 57. In embodiments, the gripping portion 54 of the second jaw 42 is configured to have one prong less than the number of prongs provided on the gripping portion 48 of the first jaw 40. In embodiments, the plurality of prongs 51a, 51b of the first jaw 40 are provided on a first end segment 49 of the gripping portion 48 of the first jaw 40, and a prong 57 of the second jaw 42 is provided on a second end segment 55 of the second jaw 42.

In one embodiment, a width W4 of the first jaw 40 at the first end segment 49 of the gripping portion 48 is greater than the width W3. In one embodiment, a width W5 of the second jaw 42 at the second end segment 55 of the gripping portion 54 is greater than the width W3. In one embodiment, the width W4 is greater than the width W5. The widths of the first and second end segments 49, 55 can be varied, such as, but not exclusively, to accommodate a specific desired number of prongs.

FIG. 7A is a cross section taken along the line A-A indicated in FIG. 7 showing a cross-section of the gripping portion 48 of one embodiment. FIG. 7A also indicates the width W3 and the thickness T3 of the gripping portion 48 at line A-A of FIG. 7. In one embodiment, edges 56, 58 of the first jaw 40 and the second jaw 42 are rounded during manufacturing so as to be smooth.

FIG. 8 is a top view of one embodiment of the grasping head 38, corresponding to the final shape shown in FIG. 4, including the blank being folded at the connecting portions 44, 50 along the centerline CL (indicated in FIG. 7). In the view of FIG. 8, the second jaw 42 is located "on top" of the first jaw 40, the first jaw therefore not being visible in the view of FIG. 8, except for some of the end segment 49 including the prongs 51, 51b. It is to be understood that in the view of FIG. 8, the prongs 51a, 51b and 57 have been shaped into the configuration indicated in FIG. 4 wherein they are generally perpendicular to a longitudinal LA axis extending through the connecting portion 44, 50. In the view of FIG. 8, the prong 57 of the second jaw 42 is to be understood as pointing away from the observer, into the plane of the paper. In one embodiment, the at least one prong 57 of the second jaw 42 is configured to fit between two neighboring prongs 51a, 51b of the first jaw 40 in the closed state. In one embodiment, the prongs 51a, 51b and 57 of the first and second jaws 40, 42 are configured to engage with each other and effectively prevent a stent to be removed from disengaging from the grasping head 38 in the closed state. In embodiments, an engagement between the prongs 51a, 51b of the first jaw 40 and the prong 57 of the second jaw 42 provides friction between the first and the second jaws which friction helps provide additional holding force of the tool 20.

Figure 9:
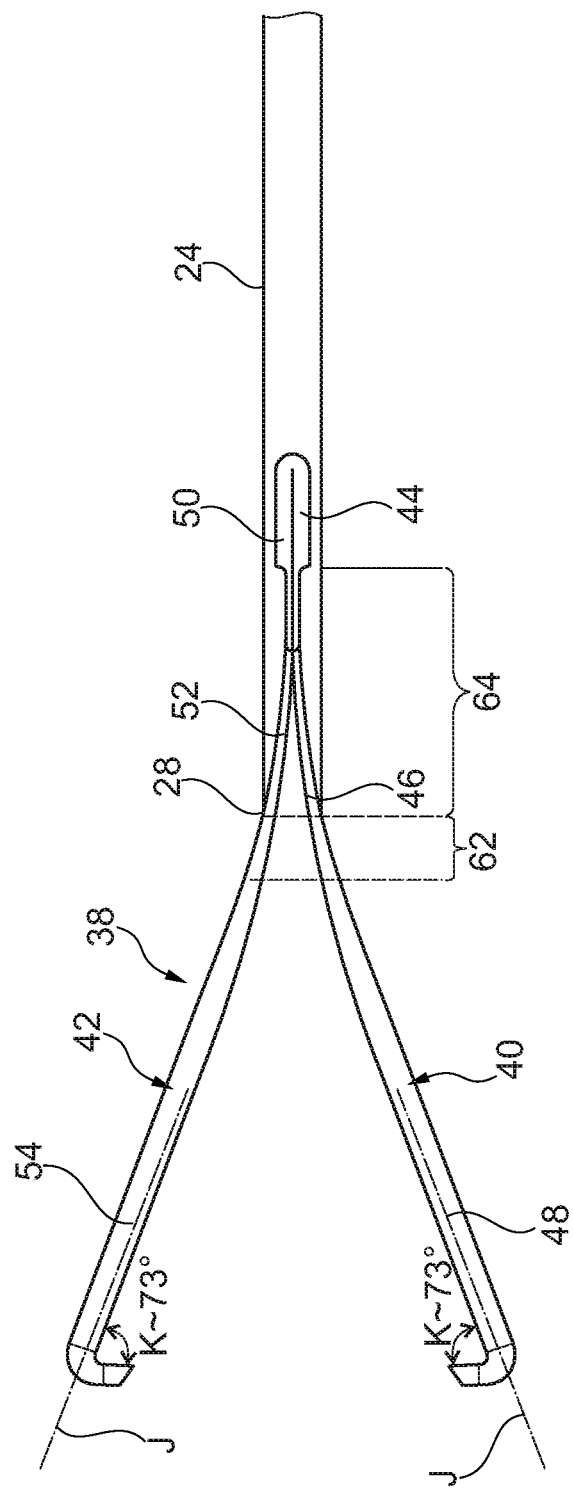
FIG. 9 is a side view of one embodiment of a grasping head.

FIG. 9 is a side view of one embodiment of the grasping head 38 at the distal end 28 of the sheath 24 in an open state of the tool. In one embodiment, in an open state position, the grasping head 38 locates such that an entirety of the gripping portion 48, 54 and at least some 62 of the intermediate portion 46, 52 is located beyond the distal end 28 of the sheath 24. In other words, in one embodiment, when the grasping head 38 is extended from the sheath 24, a portion 62 of the intermediate portion 48, 54 of the first jaw 40 and the second jaw 42 locates outside the distal end 28 of the sheath 24, while a remaining portion 64 is located within the sheath 24. In one embodiment, one or more prongs 51a, 51b, 57 of a respective first and second jaw 40, 42 extend in a direction away from a longitudinal axis J of the gripping portion 48, 54 at an angle K, measured between a prong 51a, 51b, 57 and the longitudinal axis J, of approximately 73 degrees. Production tolerances of +/−3 degrees of the angle K are acceptable.

FIG. 10 is a side view of one embodiment of the grasping head 38 located at the distal end 28 of, and generally within, the sheath 24 in the closed state. In one embodiment, the distal end 34 of the motion transfer member 30 is connected to the connecting portion 44, 50 of the grasping head. In one embodiment, a stop 66 is provided at the distal end 34 of the motion transfer member 30 and configured to stop or control the distance that the grasping head 38 is retractable into the sheath 24. The details of the stop 66 is disclosed in further detail below with respect to FIG. 11. In one embodiment, in a closed state position, the grasping head 38 locates in the sheath 24 such that an entirety of the connecting portion 44, 50, an entirety of the intermediate portion 46, 52 and at least some 68 of the gripping portion 48, 54 is located within the sheath 24. In other words, in one embodiment, when the grasping head 38 is retracted to the full extent controlled by the provision of the stop 66, a portion 70 of the gripping portion 48, 54 of the first jaw 40 and the second jaw 42 locates outside, or extends beyond, the distal end 28 of the sheath 24.

FIG. 10A is an enlarged end view of one embodiment seen from the distal direction towards the proximal direction at the distal end 28 of the sheath 24 in the closed state such as in the view of FIG. 10. In one embodiment, a first external surface 72 of the first jaw 40 and a second external surface 74 of the second jaw 42 is configured to engage with an internal surface 76 of the distal end 28 of the sheath 24 during shifting from the open state to the closed state, or vice versa. In one embodiment, each one of the first external surface 72 of the first jaw 40 and the second external surface 74 of the second jaw 42 is configured to engage with the internal surface 76 of the sheath 24 at two engagement points 78, 80 and 82, 84. In one embodiment, in the open state the first external surface 72 of the first jaw 40 and the second external surface 74 of the second jaw 42 is an external surface of the intermediate portion 46, 52 of the respective first and second jaw 40, 42 (see FIG. 9).

In one embodiment, in the open state, a first external surface 86 (see FIG. 6) of the tapering zone 60 of the intermediate portion 46 of the first jaw 40, and a second external surface 86 of the tapering zone 60 of the intermediate portion 52 of the second jaw 42 engage with an internal surface 76 of the distal end 28 of the sheath 24.

In one embodiment, the distal end 28 of the sheath 24 is configured such that engagement between the first and second external surface 86 of the tapering zone 60 of the respective first and second jaw 40, 42 and the internal surface 76 of the distal end 28 happens at two engagement points 78, 80 and 82, 84, respectively. Providing the engagement between the external surfaces 72, 74 of the jaws 40, 42 and the internal surface 76 of the sheath 24 at two engagement points, further helps reducing the force required to overcome the friction between the jaw sections and the sheath. In embodiments, locating the external surface 86 of the tapering zone 60 of the intermediate portion at two engagement points with the sheath in the open state, further helps reducing the force required to overcome static friction between the engaging parts when initiating a shifting from the open state to the closed state.

During shifting from the open state to the closed state, in one embodiment the part of the external surface 72, 74 of the jaw 40, 42 engaging with the internal surface 76 of the sheath 24 shifts (moves) from being an external surface of the intermediate portion 46, 52 to being an external surface of the gripping portion 48, 54. During shifting from the closed to the open state, the order is reversed, i.e. the location of the engagement between the external surface 72, 74 and the internal surface 76 is initially on an external surface of the gripping portion 48, 54 followed by the engagement being at an external surface of the intermediate portion 46, 52. In other embodiments, the grasping head 38 and the distal end 28 of the sheath 24 is configured to provide the engagement between the jaws 40, 42 and the internal surface 76 at an external surface 72, 74 of the gripping portion 48, 54 alone. The specific location on the external surface 72, 74 for engagement with the internal surface 76 helps control a desired gripping force of the grasping tool 38 and also helps determine what size of stent can be removed with the grasping tool 38. In embodiments, the grasping tool 38 is adapted to grip stents having a French size FR (sometimes abbreviated CH) of 4.8-9, corresponding to Ø1.6 mm-Ø3 mm.

In one embodiment, the grasping head 38 is configured to be completely retracted into the sheath 24 in the closed state. In the closed state of this embodiment, an engagement between an external surface 72, 74 of the jaws 40, 42 and the internal surface 76 will be located at an external surface of the first end segment 49 (FIG. 7) of the gripping portion 48, 54. This is advantageous in that it helps provide a grasping tool that can be advanced and retracted to and from a working position in a body cavity or canal of a patient in a more expedient manner and simultaneously avoiding contact with tissue not relevant to the procedure during movement of the tool.

Figure 11:
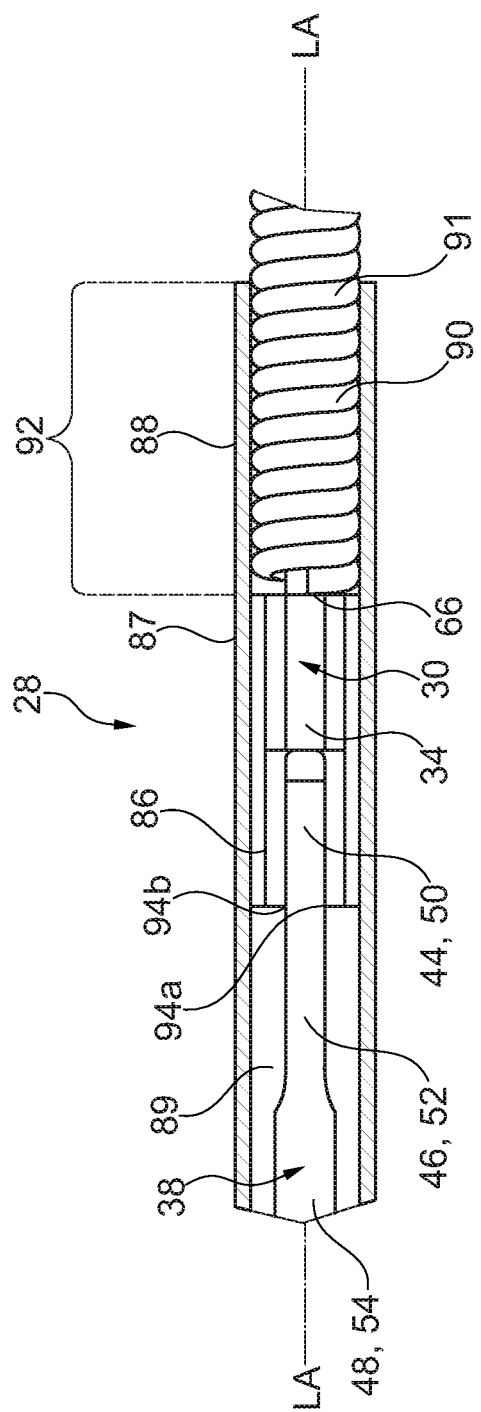
FIG. 11 is a side view of one embodiment of a distal end of a sheath of the grasping tool.

FIG. 11 is a cross-sectional view of one embodiment of the distal end 28 of the sheath 24. FIG. 11 also illustrates details of the connection between the grasping head 38 and the second distal end 34 of the motion transfer member 30. In one embodiment, a distal portion of a connecting tube 86 is welded to the connecting portion 44, 50 of the first and second jaws of the grasping head and a proximal portion of the connecting tube 86 is welded to the distal end 34 of the motion transfer member 30. In one embodiment, an outer diameter of the connecting tube 86 is configured to allow the connecting tube 86 to move linearly along longitudinal axis LA within the distal end 28 of the sheath 24, i.e. the outer diameter of the connecting tube 86 is slightly less than an inner diameter of the sheath 24. The distal end 28 of the sheath 24 defines a space 89 for the linear movement of the connected grasping head 38 and the connecting tube 86. In one embodiment, the sheath 24 includes a grasper sleeve 88. In one embodiment, the grasper sleeve 88 is located at the distal end 28 of the sheath 24. In one embodiment, the grasper sleeve 88 provides less than an entirety of the sheath 24 between the first distal end 28 and the first proximal end 26 of the sheath 24. In another embodiment, the grasper sleeve 88 provides an entirety of the sheath 24 between the first distal end 28 and the first proximal end 26.

In one embodiment, which will be explained further with respect to FIG. 12, the sheath 24 includes a plurality of components configured to provide an entirety of the sheath 24 between the first proximal end 26 and the first distal end 28. Referring to FIG. 11, in one embodiment, the outer diameter of the connecting tube 86 is greater than an inner diameter of a sheath component 90 such that a proximal portion 87 of the connecting tube 86 provides a stop 66 at a distal end of the sheath component 90. In one embodiment, the component 90 of the sheath 24 includes a round coil 91 within which the motion transfer member 30 can move. The stop 66 controls the degree to which the grasping head can be retracted into the grasper sleeve 88 when the motion transfer member 30 is moved in the proximal direction. In one embodiment, the grasper sleeve 88 is welded to the round coil 91 along an overlap 92 between them. In one embodiment, the connecting portion 44, 50 is welded to the connecting tube 86 at 94a, 94b to close off the distal portion of the connecting tube 86.

Figure 12:
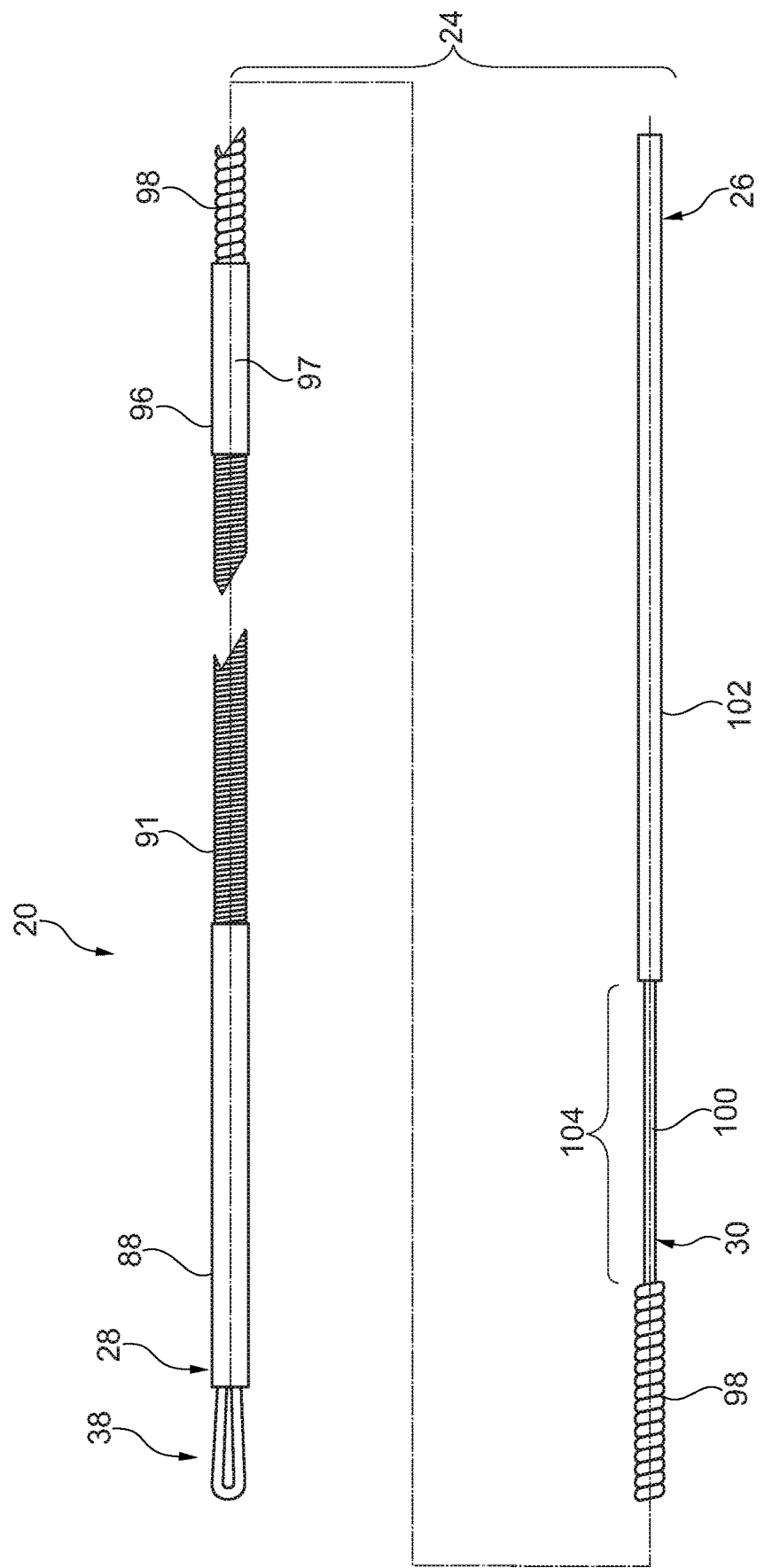
FIG. 12 is an enlarged side view illustrating a sheath, a motion transfer member and a grasping head of one embodiment of the grasping tool.

FIG. 12 is an enlarged side view illustrating a sheath 24, a motion transfer member 30 and a grasping head 38 of one embodiment of the grasping tool 20. In one embodiment, a plurality of components of the sheath 24 includes a grasper sleeve 88, a round coil 91, a flat coil 98, a coil sleeve 96 and an end sleeve 102. In one embodiment, the coil sleeve 96 is provided around the coils 96, 98 at a transition 97 between the coils. The coil sleeve 96 connects the round coil 91 and the flat coil 98. In one embodiment, the coil sleeve 96 is welded to the round coil 91 and to the flat coil 98. In one embodiment, a proximal end of the grasper sleeve 88 is welded to the round coil 91. In one embodiment, the end sleeve 102 is configured to be located at the first proximal end 26 of the sheath 24 and extends distally at least a partway towards engagement with another one of the plurality of components 88, 91, 96, 98 of the sheath 24.

In one embodiment, the flat coil 98 is provided distal to the end sleeve 102, and the round coil 91 is provided distal to the flat coil 96, with the coil sleeve 96 connecting the two coils 91, 98, and the grasper sleeve 88 connected to and extending from a distal end of the round coil 91. By virtue of their cross-sectional profiles, the flat coil component 98 provides for a stiffer or more rigid section of the sheath 24 and the round coil 91 provides for a more pliable, less rigid section of the sheath 24. Configuring the round, more flexible coil 91 distal to the flat, more rigid coil 98 of the sheath 24 helps provide optimized handling of the tool 20 such as during insertion into a body canal or cavity. In embodiments, the different components of the sheath are configured to have different individual bending and tension properties. In embodiments, the individual components are configured to have different individual inner diameters. In embodiments, individual lengths of the components 88, 91, 96, 98, 102 making up the sheath 24 are selected to meet different specifications (such as but not limited to more or less flexibility) dependent on the particular use of the grasping tool 20.

In one embodiment, the motion transfer member 30 is an inner wire 100 linearly movable within the plurality of components 88, 91, 96, 98, 102 making up the sheath 24. In one embodiment, the flat coil 98 and the end sleeve 102 do not engage, thereby providing an open zone 104 along the sheath 24 making the inner wire 100 accessible. In one embodiment, a proximal end of the inner wire 100 is connected to the tool-operating member 36.

Figure 13:
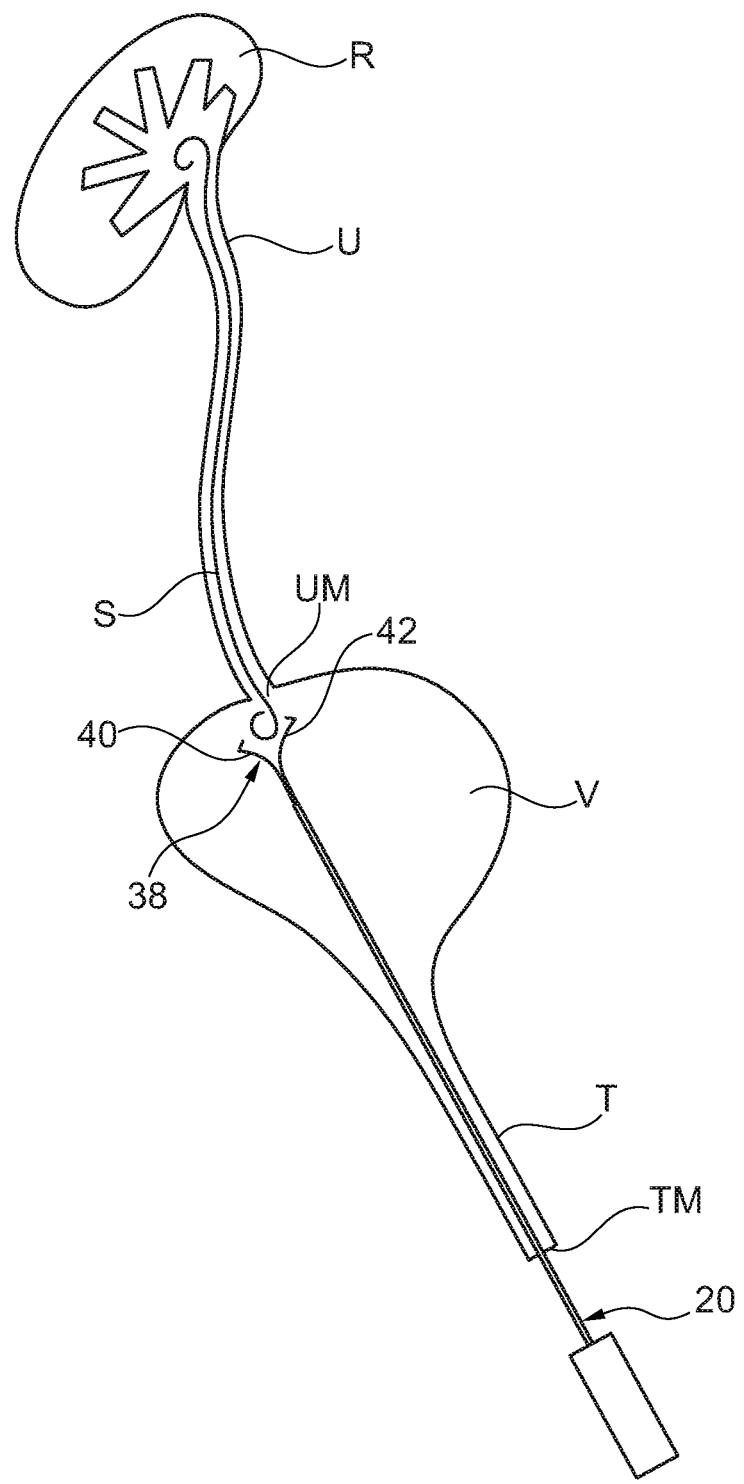
FIGS. 13 and 14 are schematic views illustrating use of the grasping tool to remove a stent from a body cavity of a patient.
Figure 14:
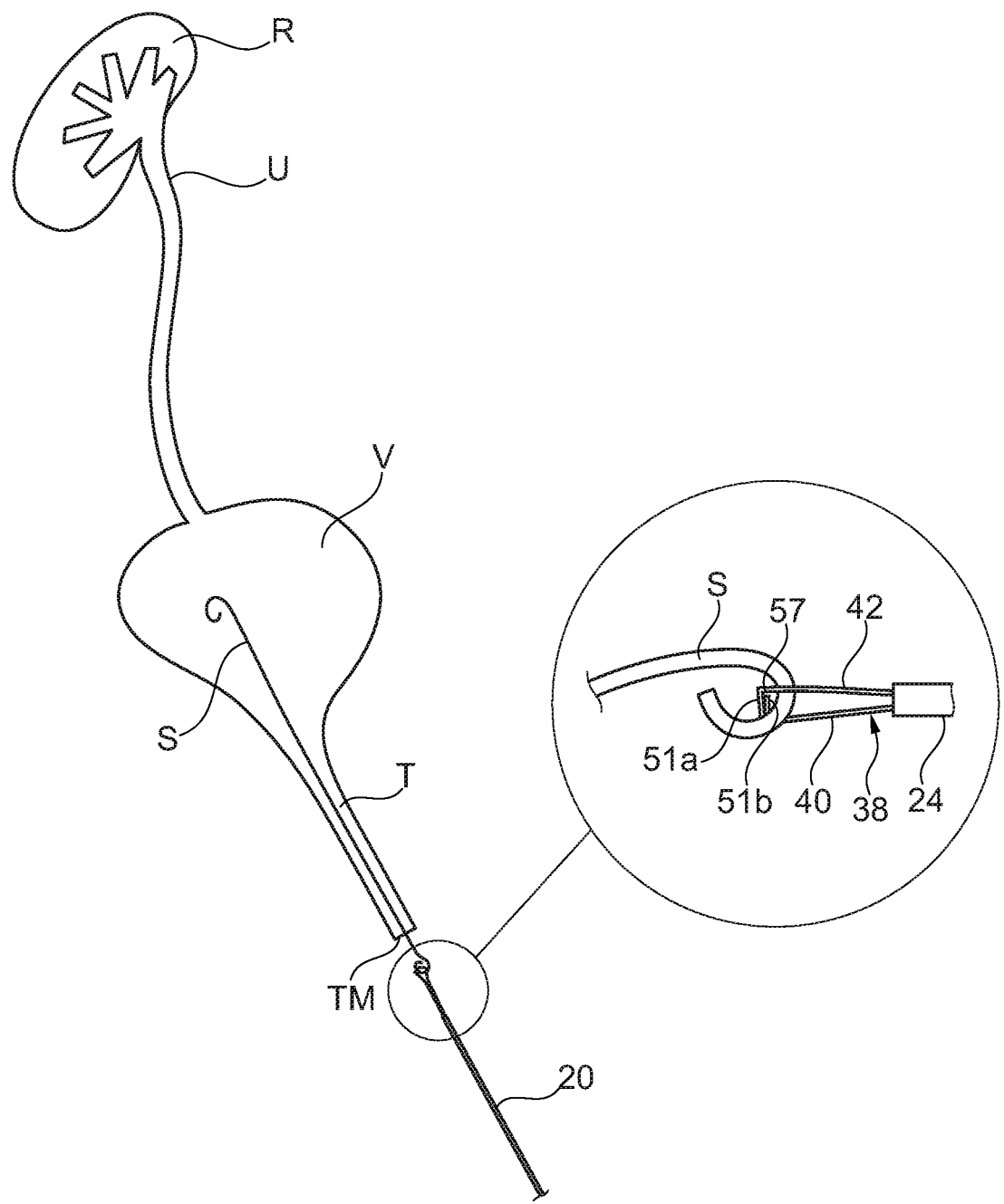

FIGS. 13 and 14 are schematic views illustrating a use of the grasping tool 20 to remove a stent from a body cavity of a patient. In the illustrated exemplary use of the tool 20 in FIGS. 13 and 14, the tool 20 is used for removal of a ureteral stent S, such as, but not limited to, a JJ- or pigtail-stent, located in a ureter U of the patient between the kidney R and the bladder V. In the illustrated example, one of the "pigtails" of the stent S is located in the bladder V just outside of a ureteral meatus UM. In the example, the grasping tool 20 is first inserted at the urethral meatus TM and advanced through the urethra T into the patient's bladder V. The grasping tool 20 further operates to extend the grasping head 38 from the distal end of the sheath and to open the jaws 40, 42 and position them around a suitable gripping location on the stent S. The grasping tool 20 then operates to firmly close the jaws 40, 42 around the stent S. The grasping tool 20 now engaged with the stent S is retracted via the bladder V and the urethra T such that the stent S is removed. FIG. 14 illustrates a situation in which the grasping tool 20 itself has been retracted to a position just outside the urethral meatus TM while a majority of the stent S has not left the urinary tract of the patient. An enlarged detail in FIG. 14 illustrates the gripping of the stent S by the jaws 40, 42 of the grasping head 38. The stent S is maintained in a firm hold by the grasping head 38 when the tool 20 is in the closed state. The prongs 51a, 51b of the first jaw 40 and the prong 57 of the second jaw engage to assist in keeping the stent S firmly secured from escaping the grip of the jaws 40, 42.

In one advantageous implementation, the grasping tool 20 is coupled to an endoscope that is inserted into the bladder V through the urethra T and used for locating a suitable gripping location on the stent S. In other implementations, the grasping tool 20 is independent of an endoscope or other surgical devices and can be positioned without the use of an endoscope, such as, but not limited to, by providing one or more radio opaque markers on the tool 20 and subjecting the patient to radiation during the procedure.

Figure 15:
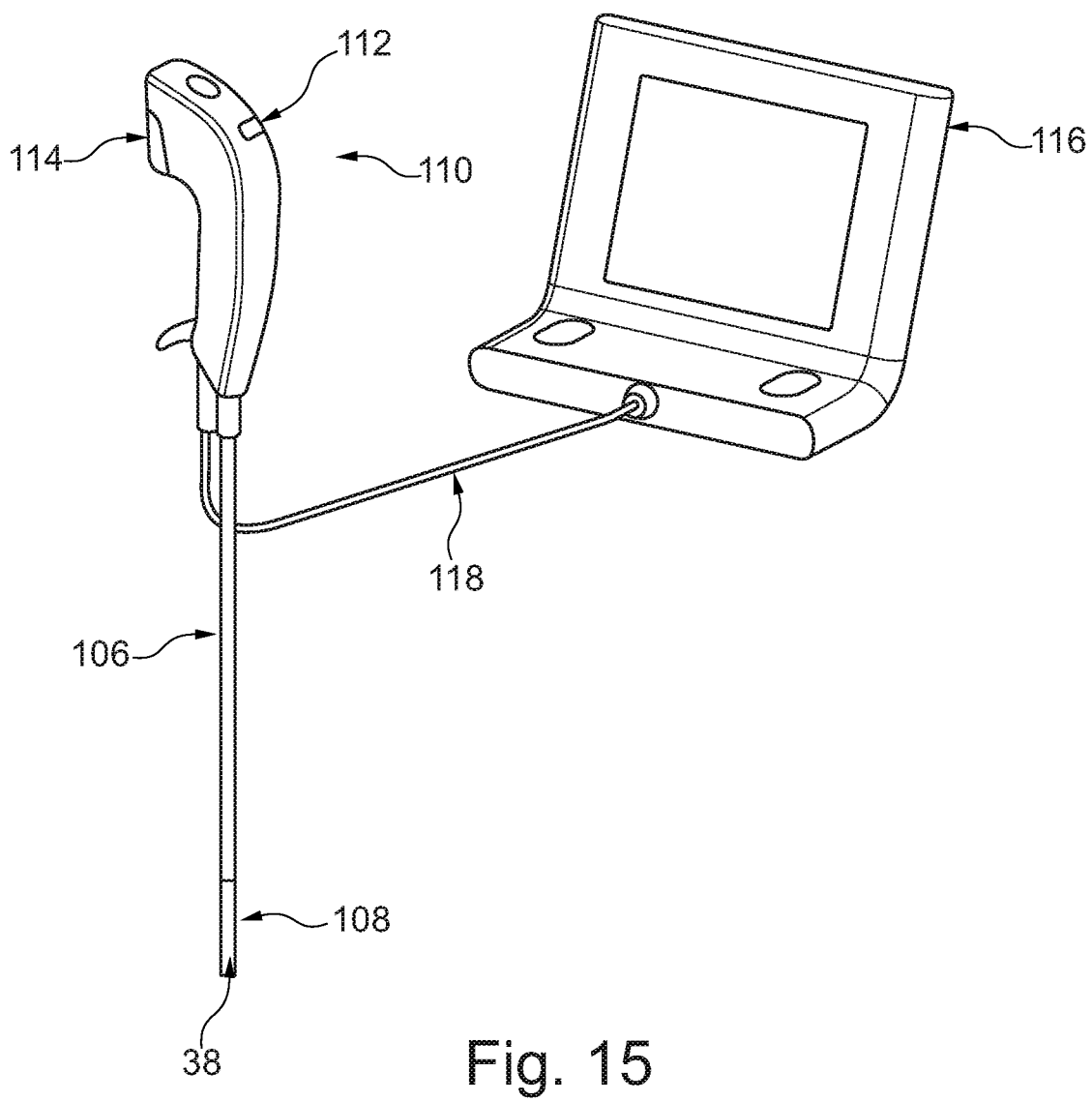
FIG. 15 is a schematic view of an exemplary system for removing a stent from a patient including a grasping tool coupled to an endoscope.

FIG. 15 is a schematic view of an exemplary system including a grasping tool 20 coupled to an endoscope 106. Only a small portion of the grasping head 38 of the grasping tool 20 is visible at a distal end 108 of the endoscope 106. The endoscope 106 includes a handle housing 110 including one or more tool operating members 112, 114. At the handle housing 110, the endoscope is connected to a monitor 116 via a cable 118.

In one aspect, the present disclosure relates to a method of removing a stent from a patient.

Figure 16:
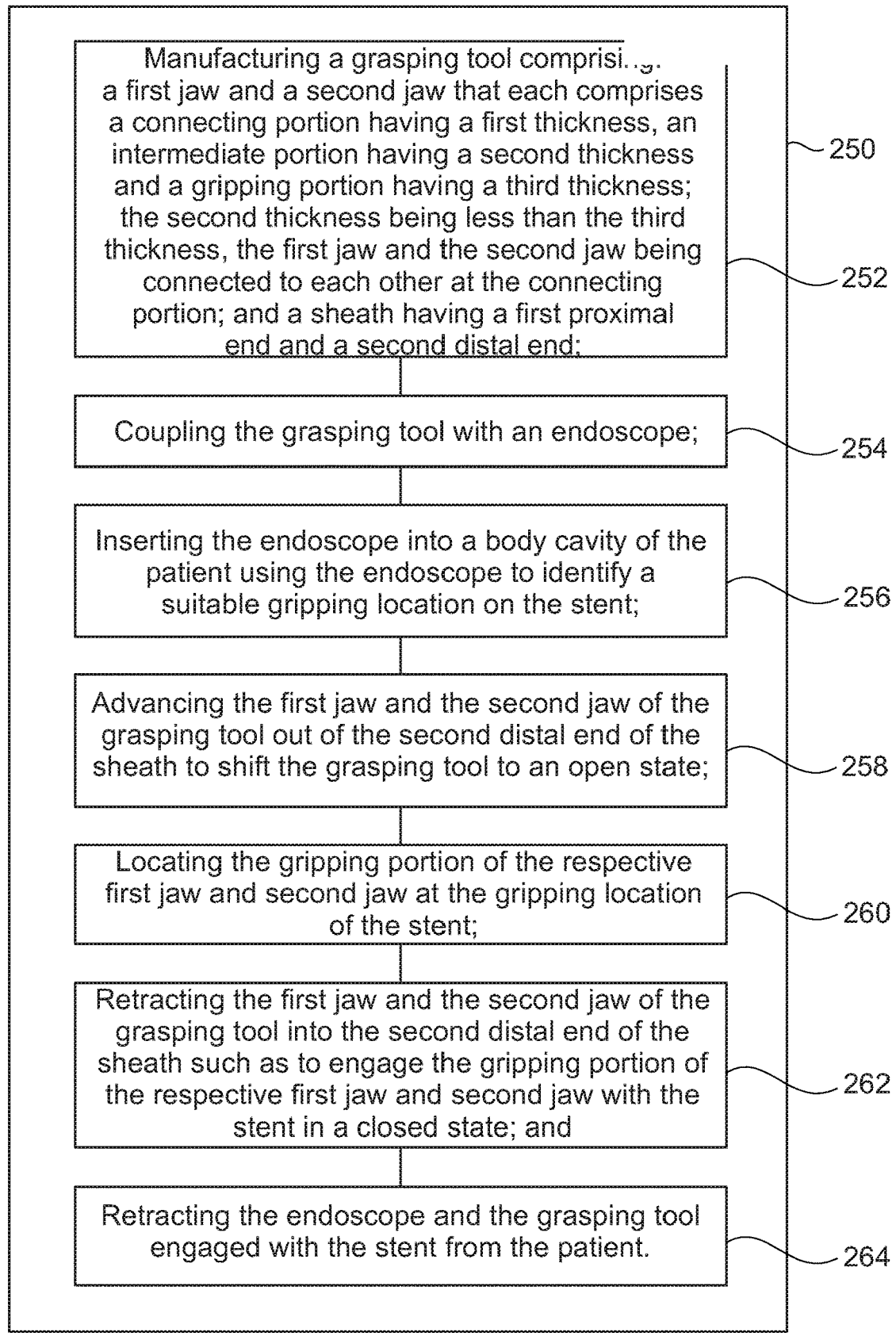
FIG. 16 is a box diagram illustrating one embodiment of a method of removing a stent from a patient.

FIG. 16 is a box diagram view illustrating one embodiment of the method of removing a stent from a patient at 252 including manufacturing a grasping tool 20. The grasping tool includes a first jaw 40 and a second jaw 42. Each jaw 40, 42 comprises a connecting portion 44, 50 having a first thickness, an intermediate portion 46, 52 having a second thickness and a gripping portion 48, 54 having a third thickness. The second thickness T2 is less (or smaller) than the third thickness T3. The first jaw 40 and the second jaw 42 are connected to each other at the connecting portion 44, 50. The grasping tool 20 also includes a sheath 24 having a first proximal end 26 and a second distal end 28.

At 254, the method includes coupling the grasping tool 20 with an endoscope. In embodiments, the grasping tool 20 is configured to move within an insertion tube of the endoscope. The grasping tool 20 can be advanced, retracted and actuated (the jaws can be opened and closed) via controls on a handle of the endoscope. In one embodiment, the coupling of the endoscope and the grasping tool 20 is carried out a manufacture so as to offer a combined instrument to users. In another embodiment, the endoscope and the grasping tool are offered separately to users, whereby the coupling of the endoscope and the grasping tool is carried out by the health care professional in preparation for the procedure for removal of the stent.

At 256, the method includes inserting the endoscope (coupled with the grasping tool 20) into a body cavity of the patient using the endoscope to identify a suitable gripping location on the stent. In one embodiment, the method includes inserting the endoscope via a urethra into a bladder or a ureter of the patient. At 258, the method includes advancing the first jaw 40 and the second jaw 42 of the grasping tool 20 out of the second distal end 28 of the sheath 24 to shift the grasping tool 20 to an open state. No longer confined by the sheath 24, the jaws 40, 42 are configured to move away from each other and open up. At 260, the method includes locating the gripping portion 48, 54 of the respective first and second jaw 40, 42 at the gripping location of the stent.

At 262, the method includes retracting the first jaw 40 and the second jaw 42 of the grasping tool 20 into the second distal end 28 of the sheath 24 such as to engage the gripping portion 48, 54 of the respective first jaw 40 and second jaw 42 with the stent in a closed state.

At 264, the method includes retracting the endoscope and the grasping tool engaged with the stent from the patient. In one embodiment, the method includes removing a ureteral stent by retracting the endoscope and grasping tool engaged with the ureteral stent out via the patient's urethra.

Figure 17:
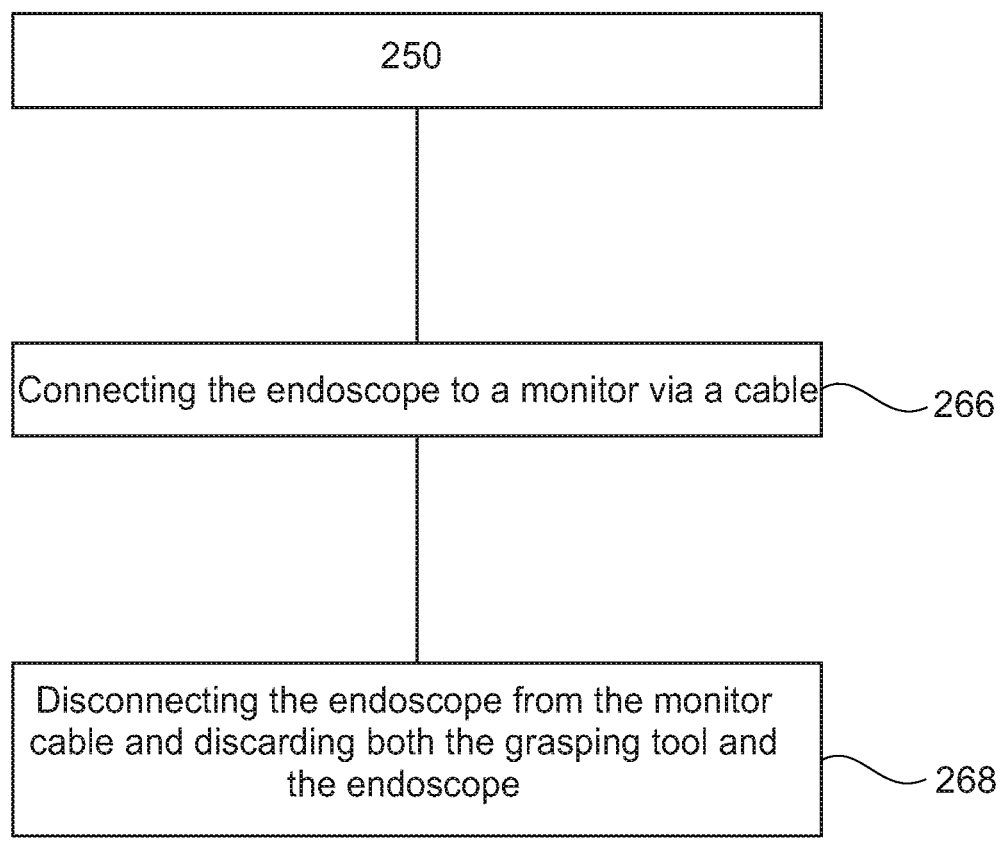
FIG. 17 is a box diagram illustrating embodiments of a method of removing a stent from a patient.

FIG. 17 is a box diagram view illustrating further embodiments of the method of removing a stent from a patient. In one embodiment, at 266, the method includes connecting the separate handle housing to a monitor via a cable. In one embodiment, at 268, the method includes disconnecting the endoscope from the separate handle housing and discarding both the grasping tool 20 and the endoscope. In one embodiment, the endoscope and the grasping tool are discarded in a container for bio-hazardous materials.

The grasping tool presented in this disclosure is configured to obtain sufficient holding force of the jaws to close around and secure a stent while requiring reduced operating force to shift the tool from the open state to the closed state. Reducing the necessary force to shift the tool from the open state to the closed state, while maintaining sufficient holding force, allows for the tool components, particularly force transferring or moving components, to be of reduced dimensions and/or made from lightweight (less bulky) materials. In the case of a grasping tool being coupled to an endoscope, the reduced force necessary to operate the tool similarly allows for the components of the endoscope to be of reduced dimensions and/or made from lightweight materials. This is turn allows the grasping tool and the endoscope to be of relatively low-cost, thus providing for single-use of these. This is particularly advantageous in that it provides for a much more efficient and cost-reduced surgical procedure by eliminating the need for repeated sterilizations of the endoscope and the tool (as single-use products, the endoscope and the grasping tool are one-time sterilized at manufacture before being supplied to users). Providing a single-use endoscope and tool also helps reduce risk of cross-contamination between patients and reduce bottlenecks in equipment availability.

As the endoscope and tool allows single handed use of the endoscope, methods of operation can be obtained in which a single health care professional can operate the endoscope and tool, thereby reducing the number of staff required to carry out a proce-dure, in turn providing easier access to the procedure and reduce the costs involved.

What is claimed is:

1. A grasping tool for removing a stent from a patient, the grasping tool comprising:
    a handle housing forming a proximal portion of the grasping tool;
    a sheath having a first proximal end and a first distal end, with the sheath having an internal surface and an external surface, with the external surface sized for insertion into a urethra and defining an outermost surface of a distal end portion of the grasping tool;

a motion transfer member movable within the sheath and having a second proximal end and a second distal end, the second proximal end connected to a tool operating member provided on the handle housing and the second distal end connected to a grasping head;

wherein the grasping head comprises a first jaw and a second jaw, where the first jaw and the second jaw are configured to be shifted between a closed state and an open state by actuating the tool operating member;

wherein each of the first jaw and the second jaw comprises a connecting portion having a first thickness, an intermediate portion having a second thickness and a gripping portion having a third thickness, where the gripping portion of the first jaw and the gripping portion of the second jaw each terminate at a tooth prong adapted to grasp a ureteral stent, wherein an internal surface of each intermediate portion, evaluated to extend an entire length from the tooth prong along the internal surface to the connecting portion, is planar on each of the first jaw and the second jaw, wherein an external surface of each intermediate portion has a tapered portion tapering from a thinner region of the second thickness of each intermediate portion to a thicker region of the third thickness of each gripping portion, with the first jaw and the second jaw connected to each other at the connecting portion;

a connecting tube connected between the grasping head and the motion transfer member, where the connecting tube is movable within the sheath; and wherein a stop is located inside of the sheath to limit axial movement of the connecting tube in a proximal direction and to control retraction of the grasping head into the sheath.

2. The grasping tool according to claim 1, wherein the first proximal end of the sheath is connected to the handle housing.

3. The grasping tool according to claim 1, wherein the connection portion of each of the first jaw and the second jaw is connected to the second distal end of the motion transfer member.

4. The grasping tool according to claim 1, wherein the first thickness of each connecting portion and the third thickness of each gripping portion is substantially identical.

5. The grasping tool according to claim 1, wherein a thickness of each jaw transitions from the second thickness to the third thickness along the tapered portion.

6. The grasping tool according to claim 1, wherein, in the closed state, an entirety of the connecting portion, an entirety of the intermediate portion, and at least a portion of the gripping portion of the first jaw and the second jaw is located within the sheath.

7. The grasping tool according to claim 1, wherein, in the open state, an entirety of the gripping portion and at least a portion of the intermediate portion of the first jaw and the second jaw is located beyond the distal end of the sheath.

8. The grasping tool according to claim 1, wherein the gripping portion of the first jaw is configured to have a plurality of first prongs and the gripping portion of the second jaw is configured to have at least one additional prong.

9. The grasping tool according to claim 1, wherein the gripping portion of the first jaw has a first prong that extends in a direction away from a longitudinal axis of the gripping portion at an angle relative to the longitudinal axis of approximately 73 degrees.

10. The grasping tool according to claim 8, wherein the at least one additional prong of the second jaw is configured to fit between two neighboring prongs of the plurality of first prongs of the first jaw in the closed state.

11. The grasping tool according to claim 8, wherein the plurality of first prongs of the first jaw and the at least one additional prong of the second jaw are configured to engage with each other and effectively prevent the ureteral stent from disengaging from the grasping head in the closed state.

12. The grasping tool according to claim 1, wherein, in the open state, the external surface of each intermediate portion of the first jaw and the second jaw engage with the internal surface of the distal end of the sheath.

13. The grasping tool according to claim 1, wherein, along a longitudinal direction of the grasping head, a first length of the gripping portion exceeds a combined length of the intermediate portion and the connecting portion of the grasping head.

14. The grasping tool according to claim 1, wherein a first length of the gripping portion in a longitudinal direction of the grasping head is 4-6 times a third length of the connecting portion, and a second length of the intermediate portion is 2-4 times the third length of the connecting portion.

15. The grasping tool according to claim 1, wherein the sheath comprises a grasper sleeve.

16. The grasping tool according to claim 15, wherein the grasper sleeve provides less than an entirety of the sheath between the first distal end and the first proximal end.

17. The grasping tool according to claim 15, wherein the grasper sleeve provides an entirety of the sheath between the first distal end and the first proximal end.

18. The grasping tool according to claim 1, wherein the sheath comprises a plurality of components located between the first proximal end and the first distal end.

19. The grasping tool according to claim 18, wherein the plurality of components comprises a grasper sleeve, a round coil, a flat coil, a coil sleeve provided around the round coil and the flat coil at a transition between the round coil and the flat coil, and an end sleeve.

20. The grasping tool according to claim 19, wherein the end sleeve is located at the first proximal end of the sheath.

21. The grasping tool according to claim 1, further comprising:
a tapered zone tapering from a thinner region of the second thickness of each intermediate portion to a thicker region of the third thickness of each gripping portion.

22. A ureteral stent grasper having a sheath that insertable into a urethra, the ureteral stent grasper comprising:
a grasping head comprising movable jaws including a first jaw connected to a second jaw, with the grasping head movable into the sheath in a distal direction to close the movable jaws and the grasping head movable out of the sheath in a proximal direction to open the movable jaws;

wherein each of the first jaw and the second jaw comprises a connecting portion having a first thickness, an intermediate portion having a second thickness and a gripping portion having a third thickness, where the gripping portion of the first jaw and the gripping portion of the second jaw each terminate at a tooth prong;

wherein an internal surface of each intermediate portion, evaluated to extend an entire length from the tooth prong along the internal surface to the connecting portion, is planar on each of the first jaw and the second jaw;

wherein an external surface of each intermediate portion has a tapered zone tapering from a thinner region of the second thickness of each intermediate portion to a thicker region of the third thickness of each gripping portion;

wherein the tapered zone is adapted to provide a ramp for sliding engagement with the sheath to reduce a retraction force for the grasping head when moving into the sheath.

* * * * *

UNITED STATES PATENT AND TRADEMARK OFFICE
CERTIFICATE OF CORRECTION

PATENT NO. : 11,033,287 B2
APPLICATION NO. : 15/574847
DATED : June 15, 2021
INVENTOR(S) : Matthison-Hansen et al.

Page 1 of 1

It is certified that error appears in the above-identified patent and that said Letters Patent is hereby corrected as shown below:

In the Specification

In Column 4, Line 15, delete "grasping head 48" and insert -- grasping head 38 --, therefor.

In Column 5, Line 66, delete "intermediate portion 48, 54" and insert -- intermediate portion 46, 52 --, therefor.

In Column 7, Line 19, delete "grasping tool 38" and insert -- grasping tool 20 --, therefor.

In Column 7, Line 20, delete "grasping tool 38." and insert -- grasping tool 20. --, therefor.

In Column 7, Line 21, delete "grasping tool 38" and insert -- grasping tool 20 --, therefor.

In Column 8, Line 30, delete "flat coil 96," and insert -- flat coil 98, --, therefor.

In Column 10, Line 56, delete "proce-dure" and insert -- procedure --, therefor.

In the Claims

In Column 11, Line 17, in Claim 1, delete "stent," and insert -- stent; --, therefor.

In Column 11, Line 22, in Claim 1, delete "jaw," and insert -- jaw; --, therefor.

Signed and Sealed this
Twenty-ninth Day of March, 2022

Drew Hirshfeld
*Performing the Functions and Duties of the
Under Secretary of Commerce for Intellectual Property and
Director of the United States Patent and Trademark Office*